United States Patent
Bartley et al.

(10) Patent No.: US 9,227,908 B2
(45) Date of Patent: Jan. 5, 2016

(54) TETRABROMOPHTHALIC DIESTER FLAME RETARDANTS AND THEIR PRODUCTION

(75) Inventors: David W. Bartley, West Lafayette, IN (US); Roy Pickering, Waldo, AZ (US); Thomas G. Ray, El Dorado, AZ (US)

(73) Assignee: Chemtura Corporation, Middlebury, CT (US)

( * ) Notice: Subject to any disclaimer, the term of this patent is extended or adjusted under 35 U.S.C. 154(b) by 120 days.

(21) Appl. No.: 12/980,469

(22) Filed: Dec. 29, 2010

(65) Prior Publication Data

US 2011/0166272 A1 Jul. 7, 2011

Related U.S. Application Data

(60) Provisional application No. 61/292,988, filed on Jan. 7, 2010.

(51) Int. Cl.
*C07C 69/76* (2006.01)
*C07C 67/26* (2006.01)
*C08K 5/12* (2006.01)
*C08K 5/00* (2006.01)

(52) U.S. Cl.
CPC ............... *C07C 69/76* (2013.01); *C07C 67/26* (2013.01); *C08K 5/0066* (2013.01); *C08K 5/12* (2013.01); *C08K 5/0008* (2013.01)

(58) Field of Classification Search
CPC ............................ C07C 67/26; C07C 69/76
USPC ............................ 524/288; 560/96, 83, 65, 98
See application file for complete search history.

(56) References Cited

U.S. PATENT DOCUMENTS

| | | | |
|---|---|---|---|
| 3,455,886 A | | 7/1969 | Versnel |
| 3,585,185 A | * | 6/1971 | Levis, Jr. et al. ............. 536/18.2 |
| 4,144,395 A | | 3/1979 | Murphy et al. |
| 4,468,479 A | * | 8/1984 | Barda ........................ 521/171 |
| 4,564,697 A | | 1/1986 | Sutker |
| 5,332,859 A | * | 7/1994 | Tarbit ............................... 560/83 |
| 2004/0171722 A1 | | 9/2004 | Brown et al. |
| 2007/0225517 A1 | * | 9/2007 | Feske et al. .................... 560/83 |
| 2007/0276055 A1 | * | 11/2007 | Sjerps ............................. 521/85 |
| 2012/0238657 A1 | | 9/2012 | Powell et al. |

FOREIGN PATENT DOCUMENTS

WO  WO 94/10123     5/1994
WO  WO 2009/058579 A1  5/2009

OTHER PUBLICATIONS

Albemarle Corporation Data Sheet, Saytex (R) RB-79 Flame Retardant, 2 pages, 2014.
Great Lake Solutions Technical Information; PHT4-DIOL (TM), 1 page, Oct. 21, 2010.
Great Lake Solutions Technical Information; PHT4-DIOL (TM) LV, 1 page, Oct. 21, 2010.
Relevant portion of Office Action for U.S. Appl. No. 13/402,266, Jan. 12, 2015 (pros13402266).

* cited by examiner

*Primary Examiner* — Wenwen Cai
(74) *Attorney, Agent, or Firm* — Dilworth IP LLC

(57) ABSTRACT

In a process for producing a tetrabromophthalic diester composition, a liquid reaction mixture is prepared comprising tetrabromophthalic anhydride (TBPA), a $C_2$ to $C_6$ polyhydric aliphatic alcohol (PAA) and an alkylene oxide (AO) selected from the group consisting of ethylene oxide and propylene oxide, said reaction mixture being substantially free of an organic solvent. While agitating the reaction mixture, the temperature of the reaction mixture is raised to at least 50° C. to allow the TBPA to react with the PAA and AO to produce a diester composition. The reaction is terminated when the diester composition has an acid value equal to or less than 0.25 mg KOH/gm of the diester composition.

4 Claims, No Drawings

TETRABROMOPHTHALIC DIESTER FLAME RETARDANTS AND THEIR PRODUCTION

This application claims benefit under 35 USC 119(e) of U.S. provisional application No. 61/292,988, filed Jan. 7, 2010, the disclosure of which is incorporated by reference.

FIELD

This invention relates to tetrabromophthalic diester flame retardants and their production.

BACKGROUND

Hydroxyl-terminated derivatives of tetrabromophthalic anhydride are well known flame retardants. Thus tetrabromophthalic anhydride (TBPA) has a high bromine content (68.9%), by which it or its derivatives can be used to impart flame retardancy to a variety plastic systems, such as polyurethanes and especially polyurethane foams. Particular examples of commercial flame retardants based on hydroxyl-terminated derivatives of tetrabromophthalic anhydride are PHT-Diol™ supplied by Chemtura Corporation (a mixed ester of tetrabromophthalic anhydride with diethylene glycol and propylene oxide) and Saytex® RB-79 supplied by Albemarle Corporation (a mixed ester of tetrabromophthalic anhydride with diethylene glycol and propylene glycol).

Because diesterification of TBPA is difficult using conventional esterification techniques, the art has turned to a method which involves reacting TBPA with a polyhydric alcohol (e.g. glycols) to form a half-ester and, subsequently, reacting the half-ester with an alkylene oxide such as propylene oxide or ethylene oxide to form the diester. An example of such a process is disclosed in U.S. Pat. No. 3,455,886, in which an anhydride is first reacted with a polyhydric alcohol at a temperature of 80 to 150° C. and, only when substantially all of the anhydride has reacted with the alcohol, is an epoxide added to the reaction mixture and the reaction to form the final diester completed at a temperature of 60 to 160° C.

More recently a single step, batch wise process for producing tetrabromophthalic diester compositions has been proposed in U.S. Pat. No. 5,332,859. This process comprises (a) preparing a first batch by reacting, in an inert organic solvent, normally toluene, at a temperature up to about 150° C., tetrabromophthalic anhydride (TBPA), a $C_2$ to $C_6$ polyhydric aliphatic alcohol (PAA) and an alkylene oxide (AO) selected from the group consisting of ethylene oxide and propylene oxide, said reacting being in a PAA:AO:TBPA mole ratio of 1.6-1.9:1.3-1.5:1, so as to obtain a reacted mixture including the tetrabromophthalic diester composition and the organic solvent; (b) recovering the organic solvent from the reaction mixture by distillation; (c) analyzing the recovered organic solvent to determine the level of its AO content; and (d) preparing a second batch by repeating step (a) above wherein the organic solvent used includes the recovered organic solvent from the previous batch and wherein its determined AO level is accounted for in achieving the PAA:AO:TBPA mole ratio.

The diester product of the process of the '859 patent is a viscous liquid which becomes less viscous with increasing temperature. Typically, the product has a viscosity at 25° C. ranging from 80,000 to 150,000 cps, which imposes significant problems in handling the product during processing. As a result, formulators generally have to heat the product to move it through plant equipment. In addition, they add modifiers to reduce the viscosity of their formulated products. It would therefore be desirable to develop an improved single step process for producing tetrabromophthalic diester compositions in which the viscosity of the product can be reduced.

According to the present invention, it has now been found that, by conducting the single step process of the '859 patent in the absence of the toluene solvent, a lower viscosity product can be produced. Even in the absence of the toluene solvent, the remaining raw materials form a solution that is viscous but can be stirred. Therefore, the toluene is not necessary for agitation purposes. By removing the toluene from the process entirely, the process step to distill and recover toluene from the product is also eliminated. Not only does this avoid the costs associated with the toluene removal, but also having to remove toluene at the end of the reaction appears to be important to the viscosity of the product. In particular, it is believed that holding the reaction product at toluene strip temperatures for an extended period results in further reaction of any excess alkylene oxide and hence extension of the diol side chains. As the side chains get longer, increased chain entanglement is possible which results in higher viscosity at any given temperature.

SUMMARY

In one aspect, the invention resides in a process for producing a tetrabromophthalic diester composition, the process comprising:

(a) preparing a liquid reaction mixture comprising tetrabromophthalic anhydride (TBPA), a $C_2$ to $C_6$ polyhydric aliphatic alcohol (PAA) and a $C_3$ to $C_8$ alkylene oxide (AO), said reaction mixture being substantially free of an organic solvent;

(b) while agitating the reaction mixture, raising the temperature of the reaction mixture to at least 50° C. and allowing the TBPA to react with the PAA and AO to produce a diester composition; and (c) terminating the reaction when the diester composition has an acid value equal to or less than 0.25 mg KOH/gm of diester composition.

In one embodiment, the $C_2$ to $C_6$ polyhydric aliphatic alcohol (PAA) comprises diethylene glycol and the alkylene oxide (AO) comprises propylene oxide.

Conveniently, the reaction mixture prepared in (a) has a PAA:TBPA mole ratio of about 1 to about 2.5:1.

Conveniently, the reaction mixture prepared in (a) has an AO:TBPA mole ratio of about 1.5 to about 2:1.

Conveniently, the reaction mixture also comprises potassium hydroxide in amount between about 0.001 to about 0.05 mole per mole of TBPA.

Conveniently, the reaction is terminated when the diester composition has an acid value between about 0.04 and about 0.10 mg KOH/gm of diester composition.

Conveniently, the diester composition has a viscosity of about 7,500 to about 100,000 cps at 25° C.

Conveniently, the temperature of the reaction mixture is cooled during (b) so as to maintain said temperature at or below 120° C.

Conveniently, the process further comprises:

(d) after terminating the reaction, removing unreacted alkylene oxide by evacuating the reaction mixture at a temperature of about 60 to about 90° C.

In a further aspect, the invention resides in a diester of tetrabromophthalic acid with a $C_2$ to $C_6$ polyhydric aliphatic alcohol (PAA) and a $C_3$ to $C_8$ alkylene oxide (AO) having a viscosity of about 7,500 to about 50,000 cps at 25° C.

In yet a further aspect, the invention resides in the use of the tetrabromophthalic diester composition described herein in flame retardant polymer compositions, particularly those employing polyurethanes.

DETAILED DESCRIPTION

Described herein is a diester diol of tetrabromophthalic acid, its production and its use as a flame retardant particularly, but not exclusively, for use in polyurethanes and especially polyurethane foams. The present diester diol is the reaction product of tetrabromophthalic anhydride (TBPA), a $C_2$ to $C_6$ polyhydric aliphatic alcohol (PAA), preferably diethylene glycol, and a substituted or unsubstituted $C_3$ to $C_8$ alkylene oxide (AO), preferably propylene oxide. In one practical embodiment, in which the PAA is diethylene glycol and the AO is propylene oxide, the diester diol has the following formula:

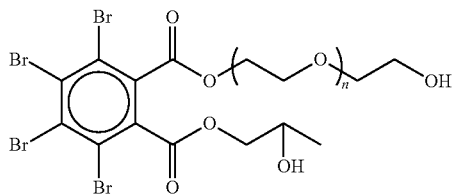

where n is typically in the range from about 1 to about 5.

The present diester diol has a viscosity at 25° C. of about 7,500 to about 100,000 cps, typically from about 7,500 to about 50,000 cps and especially from about 15,000 to about 40,000 cps, making the lower viscosity products suitable for use in foam applications that that have previously been excluded for equivalent materials with higher viscosity. In particular, in its low viscosity forms, the present diester diol is pourable at room temperature and can be pumped using standard machine pumps commonly used for spray polyurethane foam, flexible slab stock, flexible box pour, rigid discontinuous lamination panels, rigid continuous lamination panels, pour-in-place/molded applications; as well as, adhesive applications.

The present diester diol is produced in a liquid phase process in which tetrabromophthalic anhydride (TBPA) is reacted with both a $C_2$ to $C_6$ polyhydric aliphatic alcohol (PAA) and an alkylene oxide (AO) in a single stage and in the absence of an organic solvent, such as toluene. The process typically involves adding the TBPA to the PAA to form a thick, but stirrable, slurry. Potassium hydroxide is then normally added to the slurry partially to neutralize residual acid from the TBPA and partly to act as a chain extension catalyst to control the overall molecular weight and viscosity of the product. The AO is then added to slurry and the ingredients are blended together to form a homogeneous reaction mixture having the following molar composition:

| | |
|---|---|
| PAA:TBPA = | about 1 to about 2.5:1; |
| AO:TBPA = | about 1.5 to about 2.0:1; and |
| KOH:TBPA = | about 0.001 to about 0.05:1. |

The alkylene oxide (AO) can be be added in total at the beginning of the reaction, or it can be added in multiple stages, provided that at least a portion of tell overall AO is present at the beginning. For example, in one embodiment, about 20 to 35% of the AO is added at the beginning of the reaction and then after allowing a certain amount of reaction to take place, the remainder of the AO is added. In some instances each addition of the AO is gradual, e.g., over 0.2 to 5.0 hours, and in some cases, a period of time is allowed to elapse, often at elevated temperature between the first addition of a portion of the AO and the second addition of the remainder.

The amount of PAA added to the reaction mixture can be varied to adjust the viscosity of the final diester diol, with higher values within the PAA:TBPA range given above resulting in lower viscosity products. To produce a low viscosity product (about 15,000 to about 50,000 cps at 25° C.), PAA:TBPA mole ratio is generally adjusted to be in the range of about 1.5 to about 2:1

The resultant reaction mixture is then heated under stirring to a temperature of at least 50° C., generally between about 60° C. and about 65° C. to initiate the esterification reaction. Since the reaction is exothermic, the temperature may rise as the reaction proceeds and so cooling is generally applied to the reaction mixture to retain the temperature at or below 120° C. The reaction mixture is then maintained at this temperature for about 2 hours to about 8 hours to complete the reaction. The reaction is terminated when the diester composition has an acid value equal to or less than 0.25 mg KOH/gm, generally between about 0.04 and about 0.10 mg KOH/gm, of the diester composition. After the reaction has been terminated, residual propylene oxide is bled to a scrubber and the reaction mixture held under vacuum to remove volatiles.

The resultant diester diol of tetrabromophthalic acid can be used as a flame retardant for many different polymer resin systems such as polystyrene, high-impact polystyrene (HIPS), poly (acrylonitrile butadiene styrene) (ABS), polycarbonates (PC), PC-ABS blends, polyolefins, polyesters and/or polyamides and polyurethanes. Because of its thermal stability, bromine content and reactivity, the product is particularly useful as a flame retardant for polyurethanes and especially polyurethane foams. In flame retarding polyurethanes, the present diester diol is used as a reactive additive and can be present in the final formulated resin at levels of about 1% to as much as 55%. Preferably, the amounts range from 3 to 30% with a particularly preferable amount ranging from 5 to 15%.

Although the present diester diol can be used alone to enhance the flame retardant properties of a polymer composition, it may in some cases be desirable to blend the diester diol with other flame retardant materials. One particularly useful blend is with at least one hindered phenolic antioxidant since such a blend not only offers flame retardancy but also anti-scorch/anti-discoloration properties. A suitable hindered phenolic antioxidant is one in which the phenolic ring is substituted by an alkanoic acid alkyl ester group in which alkanoic acid moiety has in the range of about 2 to about 4 carbon atoms and the alkyl group has in the range of about 6 to about 16 carbon atoms. Specific examples of such hindered phenolic compounds include Anox 1315, Anox 70, Anox 330, Naugard 431, and Naugard BHT, all supplied by Chemtura Corporation. There are many other examples of phenolic antioxidants that are available from other suppliers as well. Typically the ratio of the diol ester to the hindered phenolic antioxidant is in the range of about 100:0.1 to about 100:1.

The invention will now be more particularly described with reference to the following non-limiting Examples.

EXAMPLE 1

240 grams (2.26 moles) of diethylene glycol (DEG) are loaded into a 1 liter one-piece pressure reactor equipped with a stirrer and 640 grams (1.38 moles) of tetrabromophthalic anhydride (TBPA) are slowly added to the DEG with stirring. 0.8 gram (0.014 mole) of KOH is then added to the stirred mixture followed by 152 grams (2.62 moles) of propylene oxide (PO). With continued stirring, the resultant mixture is heated to 60-65° C. at which point the mixture starts to exotherm and the temperature of the mixture increases to about 140° C. within about 5-10 minutes and the pressure in the reactor begins to rise.

External heating is removed at the onset of the exotherm and the temperature and pressure are carefully monitored during the heat-up period. If necessary, cooling is applied to the reaction mixture and/or PO is vented from the mixture if the temperature exceeds 200° C. and/or the pressure exceeds 45 psig (411 kPa). Once the reaction mixture has reached its maximum exotherm temperature, the mixture is allowed to cool back down to 120° C. and then held at this temperature for 4 hours. Stirring is continued throughout the hold period.

At the end of the 4 hour hold period, the product is allowed to cool to an appropriate temperature for handling and, when the product has cooled, the reactor seal is released, after any excess pressure has been removed by venting the reactor vapor into a sulfuric acid scrubber or trap. Stirring is now ceased and the acidity of the product is analyzed. If the acidity of the product is >0.25 mg KOH/g, additional propylene oxide is added to the product and the product is heated at 120° C. for another 0.5 hour and the acidity is rechecked. This operation is repeated until the acidity of the product is <0.25 mg KOH/g.

Once the acidity of the product has reached 0.25 mg KOH/g or less, the contents of the reactor are transferred into a 1 liter one-necked round bottom flask. The flask is then placed on a rotary evaporator and rotovapped at 75° C. at full aspirator vacuum to remove any volatiles. The resultant product is then removed for storage and use and has the properties listed in Table 1.

EXAMPLE 2

The process of Example 1 is repeated but with the reaction mixture being composed of 200 grams (1.88 moles) of DEG and 1.6 gram (0.028 mole) of KOH, the amounts of TBPA and PO remaining unchanged. A higher viscosity diester diol is produced having the properties listed in Table 1.

EXAMPLE 3

The process of Example 1 is repeated but scaled up into a 5 liter piece pressure reactor and with the reaction mixture being composed of 990 grams (9.32 moles) of DEG, 2881 grams (6.21 moles) of TBPA, 3.6 gram (0.063 mole) of KOH and 663 grams (11.43 moles) of PO. An intermediate viscosity diester diol is produced having the properties listed in Table 1.

EXAMPLE 4 (COMPARATIVE)

In this Example a route to making a diester diol of TBPA with DEG and PO is described using toluene as a solvent.

Toluene (285 gms) is charged to a 1 liter one-piece pressure reactor equipped with a stirrer and 721 grams (1.6 moles) of TBPA and 29 gram (0.5 mole) of KOH are added to the reactor with stirring. Once the TBPA has dissolved in the toluene, 234 grams (2.2 moles) of DEG and 160 grams (2.7 moles) of PO are added to the reactor. With continued stirring, the resultant mixture is heated to 55-60° C. at which point the mixture starts to exotherm and the temperature of the mixture begins to rise.

The exothermic reaction is controlled using cooling as necessary so that the temperature of the mixture does not exceed 105° C. and, once this temperature has been reached, the mixture is held at this temperature under stirring for 1 hour. Samples of the mixture are removed for acid number testing every hour and, once the acid number is within specification (<0.25 mg KOH/g), the reactor contents are heated under vacuum to start removal of the toluene solvent allowing the temperature to increase to a maximum of 120° C. After vacuum distillation for 1 hour, water is slowly added to the product mixture to improve toluene removal via azeotrope formation. After an additional 4 hours of distillation with water addition, sampling the product mixture is initiated to test for toluene levels. Once the toluene concentration is within specification (<0.10%), the water injection is turned off but stripping is continued. After 1 hour of further stripping, sampling the product mixture is initiated to test for water levels. Once the water concentration is within specification (<0.15%), stripping is discontinued and the reactor contents are recovered. The resultant product has the properties listed in Table 1.

TABLE 1

| | Example 1 | Example 2 | Example 3 | Example 4 |
|---|---|---|---|---|
| Viscosity (K cps) | 20-30 | 80-100 | 20-30 | 80-130 |
| Acidity (mg KOH/g) | 0.04-0.10 | 0.04-0.10 | 0.04-0.10 | <0.25 |
| OH number (mg KOH/g) | 225-240 | 220-225 | 225-240 | 200-235 |
| Water (ppm) | 100-400 | 100-400 | 100-400 | 2000 |

EXAMPLE 5

The process of examples 1 or 3 are repeated with the exception that after the DEG, TBPA and KOH are added, approximately 25-33% of the PO is added over the course of 0.5-1 hour after which the reaction mixture is held for 0.5 hour. During the hold time, the reaction begins to exotherm with temperatures reaching 50-90° C. After the hold, the remaining PO is added over the course of 3-4 hours. The reaction will continue to exotherm during this period and can reach temperatures of 140° C. during this phase of the addition. After the addition is completed, the reaction is continued as described in Examples 1 and 3.

While the present invention has been described and illustrated by reference to particular embodiments, those of ordinary skill in the art will appreciate that the invention lends itself to variations not necessarily illustrated herein.

We claim:
1. A process for producing a tetrabromophthalic diester diol composition, the process comprising:
   (a) preparing a liquid reaction mixture comprising tetrabromophthalic anhydride (TBPA), from about 1.5 moles to about 2.0 moles of propylene oxide per mole of TBPA, and from about 1.5 to about 2.0 moles of diethylene glycol per mole of TBPA, said reaction mixture being substantially free of an organic solvent; then,
   (b) while agitating the reaction mixture, raising the temperature of the reaction mixture to between about 60° C. and about 65° C. to initiate an exothermic reaction of TBPA with the propylene oxide and diethylene glycol to produce the diester diol composition, wherein the reaction temperature is kept at or below 120° C.; and

(c) terminating the reaction when the diester diol composition has an acid value equal to or less than 0.25 mg KOH/gm and removing volatiles under vacuum to yield the tetrabromophthalic diester diol composition,
wherein the tetrabromophthalic diester diol composition has a viscosity of about 15,000 to about 40,000 cps at 25° C. and is the reaction product of tetrabromophthalic anhydride (TBPA), propylene oxide and diethylene glycol, wherein the tetrabromophthalic diester diol has a formula of

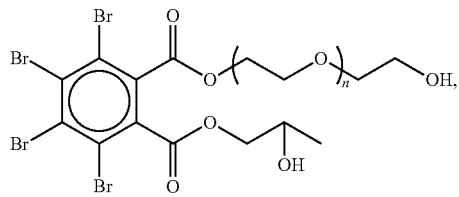

where n is from about 1 to about 5.

2. The process of claim 1, wherein the reaction mixture also comprises potassium hydroxide in an amount between about 0.001 to about 0.05 mole per mole of TBPA.

3. The process of claim 1, wherein the reaction is terminated when the diester diol composition has an acid value between about 0.04 and about 0.10 mg KOH/gm.

4. A process for producing a tetrabromophthalic diester diol composition, the process comprising:
(a) preparing a liquid reaction mixture comprising tetrabromophthalic anhydride (TBPA), propylene oxide in an amount that is 20 to 35% of the total amount ranging from about 1.5 moles to about 2.0 moles of propylene oxide per mole of TBPA, from about 1.5 to about 2.0 moles of diethylene glycol per mole of TBPA, and between about 0.001 to about 0.05 moles of potassium hydroxide per mole of TBPA, said reaction mixture being substantially free of an organic solvent; then,
(b) while agitating the reaction mixture, raising the temperature of the reaction mixture to between about 60° C. and about 65° C. to initiate an exothermic reaction of TBPA with the propylene oxide and diethylene glycol and then adding the remainder of the about 1.5 moles to about 2.0 moles of propylene oxide per mole of TBPA to the reaction mixture to produce the diester diol composition, wherein the reaction temperature is kept at or below 120° C.; and
(c) terminating the reaction when the diester diol composition has an acid value equal to or less than 0.25 mg KOH/gm and removing volatiles under vacuum to yield the tetrabromophthalic diester diol composition,
wherein the tetrabromophthalic diester composition has a viscosity of about 15,000 to about 40,000 cps at 25° C. and is the reaction product of tetrabromophthalic anhydride (TBPA), propylene oxide and diethylene glycol, wherein the tetrabromophthalic diester diol has a formula of

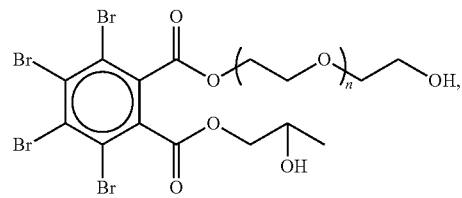

where n is from about 1 to about 5.

* * * * *